US010085454B2

(12) United States Patent
Bradbury et al.

(10) Patent No.: US 10,085,454 B2
(45) Date of Patent: Oct. 2, 2018

(54) REMEDIATION OF MOLLUSK INFESTATIONS

(71) Applicant: WISEARTH IP, INC., Plano, TX (US)

(72) Inventors: Rod S. Bradbury, Saanichton (CA); Robert Michael Lockerd, Plano, TX (US); Deborah A. Chadbourne, Bethlehem, PA (US)

(73) Assignee: WISEARTH IP, INC., Plano, TX (US)

( * ) Notice: Subject to any disclaimer, the term of this patent is extended or adjusted under 35 U.S.C. 154(b) by 46 days.

(21) Appl. No.: 14/981,103

(22) Filed: Dec. 28, 2015

(65) Prior Publication Data
US 2016/0157498 A1   Jun. 9, 2016

Related U.S. Application Data

(63) Continuation-in-part of application No. 14/244,609, filed on Apr. 3, 2014, now Pat. No. 9,220,274, which is a continuation of application No. 13/617,410, filed on Sep. 14, 2012, now Pat. No. 8,771,762.

(60) Provisional application No. 61/534,486, filed on Sep. 14, 2011.

(51) Int. Cl.
| A61K 36/00 | (2006.01) |
| A01N 65/08 | (2009.01) |
| A01N 65/00 | (2009.01) |
| B08B 9/027 | (2006.01) |
| B63J 4/00 | (2006.01) |
| C02F 1/50 | (2006.01) |
| C02F 1/68 | (2006.01) |
| C02F 103/00 | (2006.01) |

(52) U.S. Cl.
CPC .............. *A01N 65/08* (2013.01); *A01N 65/00* (2013.01); *B08B 9/027* (2013.01); *B63J 4/00* (2013.01); *C02F 1/505* (2013.01); *C02F 1/688* (2013.01); *C02F 2103/008* (2013.01); *Y02A 50/331* (2018.01)

(58) Field of Classification Search
CPC ................................................... A61K 36/00
See application file for complete search history.

(56) References Cited

U.S. PATENT DOCUMENTS

| 3,732,202 A | 5/1973 | Jewers et al. |
| 3,813,383 A | 5/1974 | Lemma et al. |
| 3,886,272 A | 5/1975 | Parkhurst et al. |
| 4,154,818 A | 5/1979 | Sadaoki et al. |
| 5,252,330 A | 10/1993 | Lee et al. |
| 5,334,386 A | 8/1994 | Lee et al. |
| 2003/0140683 A1 | 7/2003 | Aldridge et al. |
| 2006/0127435 A1 | 6/2006 | Voris |
| 2006/0182776 A1 | 8/2006 | Voris et al. |
| 2007/0196517 A1 | 8/2007 | San Martin |
| 2007/0264363 A1 | 11/2007 | Bowen et al. |
| 2009/0111694 A1 | 4/2009 | Dituro |
| 2012/0321688 A1 | 12/2012 | Crebassa et al. |
| 2013/0209372 A1 | 8/2013 | Sahin et al. |
| 2014/0220092 A1 | 8/2014 | Bradbury |

FOREIGN PATENT DOCUMENTS

| CA | 2034414 A1 | 4/1992 |
| EP | 0962136 A1 | 12/1999 |
| JP | S57188509 A | 11/1982 |
| JP | 05178701 A * | 7/1993 |
| JP | 2002154907 A | 5/2002 |
| WO | 08686 A1 | 5/1993 |
| WO | 56140 A1 | 9/2000 |

OTHER PUBLICATIONS

Lemma, Endod is lethal to zebra mussels and inhibits their attachment, Journal of Shellfish Research, (1991) vol. 10, No. 2, pp. 361-366 (Year: 1991).*
Helaly et al, Parameters affecting the migration of molluscicidal saponin from styrene butadiene rubber formulations containing Phytolacca dioica L. Journal of Saudi Chemical Society (2001), 5(2), 231-244 (Year: 2001).*
Martin et al, Use of a saponin based molluscicide to control Pomacea canaliculata snails in Southern Brazil. Natural product communications, (Oct. 2009) vol. 4, No. 10, pp. 1327-1330 (Year: 2009).*
PCT International Search Report and Written Opinion for PCT/US16/67514 dated Mar. 9, 2017 (27 pages).
Lemma, "Laboratory and Field Evaluation of the Molluscicidal Properties of Phytolacca dodecandra", Bull. Wld Hlth Org. 1970, 42, pp. 597-612.
Lemma, et al., "Studies on the Molluscicidal Properties of Endod (Phytolacca Dodecandra): I. Increased Potency With Butanol Extraction", The Journal of Parasitology, vol. 58, No. 1, Feb. 1972, pp. 104-107.
Eguale, et al. "Molluscicidal Effects of Endod (Phytolacca Dodecandra) on Fasciola Transmitting Snails" Ethiop. J. Sci. 25(2), 2002, pp. 275-284.
Lemma, "Endod is lethal to zebra mussels and inhibits their attachment," Journal of Shellfish Research, (1991) vol. 10, No. 2, pp. 361-366.

(Continued)

*Primary Examiner* — Qiuwen Mi
(74) *Attorney, Agent, or Firm* — Shaukat A. Karjeker; Carstens & Cahoon, LLP

(57) ABSTRACT

An exemplary embodiment provides a method of treating an environment (aquatic or land) to remediate an infestation of mollusks, either active or in hibernation, to remediate a mollusk infestation. The method includes the steps of: selecting an amount of a formulation (solid or liquid) comprising a saponin; and distributing this formulation in the environment having an infestation of mollusks. When the environment is land, the steps of the method may include distributing the formulation on the land, flooding the land, for example by irrigation or seasonal rains, to release the saponin that disperses in the water to thereby cause a concentration of saponin in the water for a time effective to remediate mollusks. When the environment is water, the formulation may be distributed into the water to cause a saponin concentration for an effective time to remediate mollusks.

25 Claims, 2 Drawing Sheets

(56) References Cited

OTHER PUBLICATIONS

Parkhurst et al., "Molluscicidal Saponins of Phytolacca Dodecanra: Oleanoglycotoxin-A" Phytochemistry, 1973, vol. 12, pp. 1437-1442 (6 pages).

Lambert et al., "Endod: Safety Evaluation of a Plant Molluscicide" Regulatory toxicology and Pharmacology 14, 189-201 (1991) (13 pages).

Thilborg et al., "Molluscicidal Saponins from Phytolacca Dodecandra" Phytochemistry, vol. 32, No. 5, pp. 1167-1171, 1993 (5 pages).

Parkhurst et al., "Molluscicidal Saponins of Phytolacca Dodecandra: Lemmatoxin" Can. J. Chem., 52, 702 (1974) (4 pages).

Duncan "The Toxicology of Plant Molluscicides" Pharmac. Ther. vol. 27, pp. 243-264, 1985 (22 pages).

Slacanin et al., "High-Performance Liquid Chromatographic Determination of Molluscicidl Saponins from Phytolacca Dodecandra (Phytolaccaceae)" Journal of Chromatography, 448 (1988) 265-274 (10 pages).

Domon et al., "High-Performance Liquid Chromatography of Oleanane Saponins" Journal of Chromatography, 315(91984) 441-446 (6 pages).

\* cited by examiner

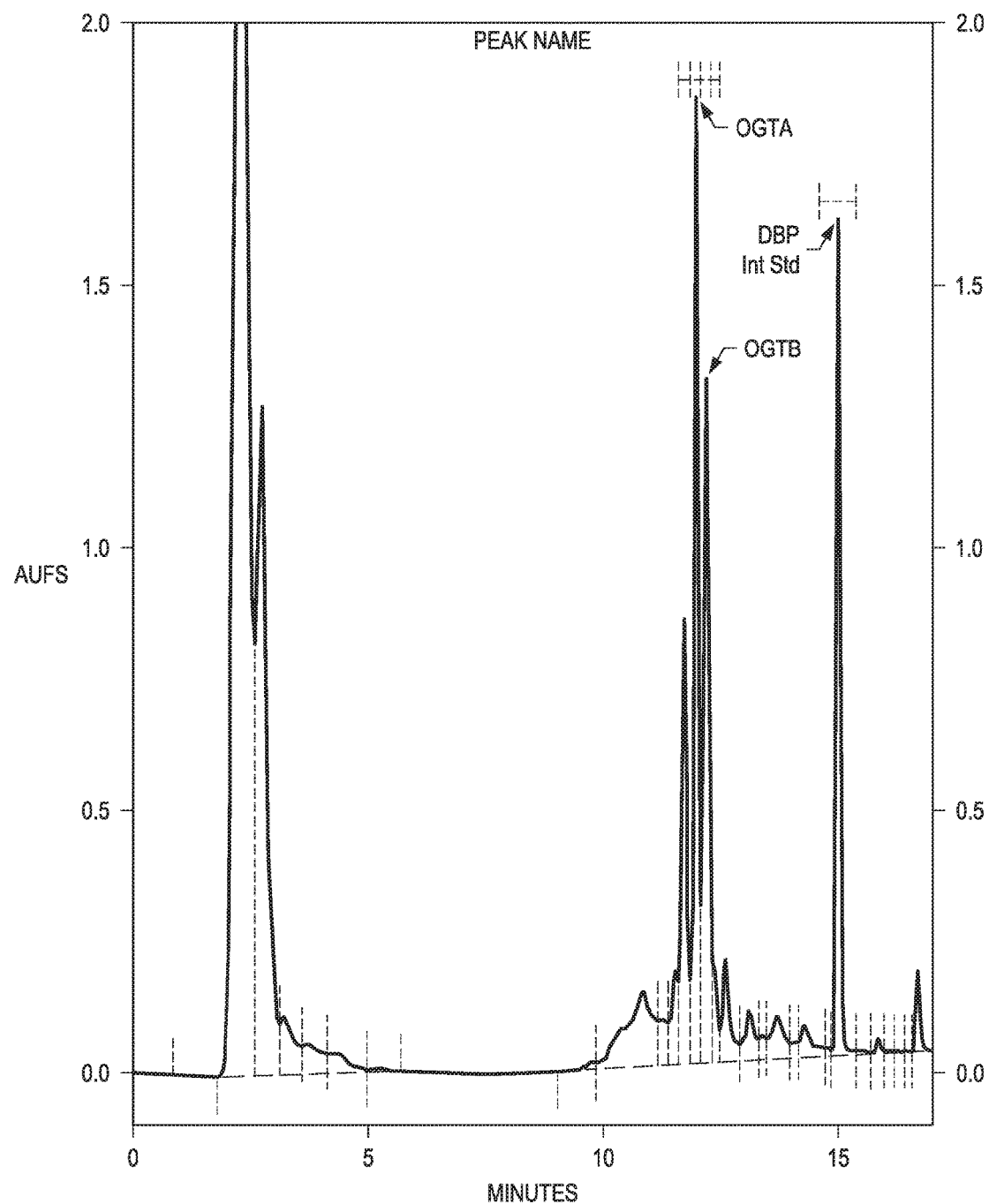

REMEDIATION OF MOLLUSK INFESTATIONS

CROSS-REFERENCE TO RELATED APPLICATION

This application is a continuation of co-pending U.S. Ser. No. 14/244.609 filed Apr. 3, 2014, which is a continuation of U.S. Ser. No. 13/617,410 filed Sep. 14, 2012, now U.S. Pat. No. 8,771,762 issued on Jul. 8, 2014, which is in turn a continuation-in-part of U.S. Provisional Patent Application Ser. No. 61/534,486, entitled "Method and Apparatus for Treating Pests," filed Sep. 14, 2011, the technical disclosures of which are hereby incorporated herein by reference.

BACKGROUND OF THE INVENTION

1. Technical Field

The present invention relates to a method and apparatus for controlling, reducing or eliminating infestations of mollusks.

2. Description of Related Art

Mollusks cause both economic harm as well as harm to human health. In terms of economic harm, mollusks such as zebra mussels (*Dreissena polymorpha*), quagga mussels (*Dreissena rostriformis bugensis*) and Asian clams (*Corbicula fluminea*) infest waterways, clog water intake pipes from water supplies, including industrial water sources. In particular, the zebra mussel, *Dreissena polymorpha*, attaches to and clusters atop virtually any solid surface. This causes blockage or severely restricted water flow when the surface is a water intake pipe as the mussels clog the flow path in the pipe. In addition, the mussels attach to ships' ballasts.

Several mollusk species are also carriers ("vectors") of debilitating diseases, such as schistosomiasis caused by flat worms of the Schistosoma type, fascioliasis caused by flat worm of the *Fasciola, Clonorchis*, and *Opisthorchis* type, paragonimiasis caused by the flatworm of the *Paragonimus* type. Some 350 snail species, especially in the genera *Biomphalaria, Bulinus, Oncomelania, Tricula*, and *Lymnaea*, are estimated to be of possible medical or veterinary importance as intermediate hosts of human parasites. Often, the disease-carrying capabilities are manifested in parts of the world that are relatively impoverished, and where public health care resources are constrained. Thus, the mollusks cause human misery over large populations, particularly in Africa and Asia.

In addition, species of mollusk attack and devour or damage vital crops. For example, the Golden Apple snails (*Pomacea canaliculata*) and the Australian rice snails (*Isidorella new combi*) are serious rice and taro crop destroying pests, respectively, in parts of South East Asia where rice is a staple food, and in Australia. The snails have the capability to hibernate underground or in protected areas and emerge when crop planting commences and the rice paddy fields are watered. (The term "aestivation" is used to describe this underground hibernation of snails. For simplicity the word hibernation will be used herein.) The snails graze on the tender young rice or taro shoots causing large crop losses. In addition, to the extent that the snails may be carriers of a disease, the laborers that work the paddy fields may become infected.

Mollusks are ubiquitous and may be found in almost any aquatic-type environment, including running water (e.g. rivers, creeks and streams), lakes and dams, industrial water treatment basins, and, as mentioned above, rice paddy fields. They multiply rapidly, have few predators, and cause economic harm as well as harm to human health.

SUMMARY

An exemplary embodiment provides a method of treating an environment having an infestation of mollusks, either active or in hibernation, to remediate a mollusk infestation. The method includes the steps of: selecting an amount of a formulation comprising a saponin; distributing the formulation in the environment having an infestation of mollusks either active or in hibernation. It also includes allowing the saponin to disperse in water in the environment to thereby cause an effective lethal concentration of saponin in the water; and maintaining an effective concentration for an exposure time sufficient to remediate the mollusk infestation.

Optionally, the step of maintaining the lethal concentration includes distributing an additional amount of the formulation, at an interval of time after the first distribution of the formulation. Optionally, the method includes maintaining an effective concentration for an exposure time of about 1 to about 48 hours. Optionally, the method includes maintaining an effective concentration for an exposure time of more than about 8 hours.

Optionally, the exemplary method includes selecting a formulation comprising saponin and a binder. Optionally, the method includes selecting a formulation comprising a synthetic saponin and a binder. Optionally, the exemplary method includes using a formulation in a solid form, exemplified by granular, powdered, pelletized and tableted forms. Optionally, the exemplary method includes using a formulation that is in a liquid form. Optionally, the exemplary method has a formulation with a time-controlled release of saponin. Optionally, the exemplary method includes using a delivery method comprising a premeasured quantity of the saponin-containing formulation.

Optionally, the exemplary method is applied when the mollusks comprise snails, and in particular, Golden Apple snails (*Pomacea canaliculata*) or Australian rice snails (*Isidorella new combi*).

Optionally, the environment comprises a rice paddy field wherein the mollusks comprise snails, and wherein the step of distributing the formulation includes distributing the formulation on the paddy field before flooding the paddy field.

Optionally, the environment comprises a rice paddy field wherein the mollusks comprise snails, and wherein the step of distributing the formulation on the paddy field is after planting rice seedlings or before emergence of rice shoots, when the paddy field is seeded.

Optionally, the method further includes a step of distributing the formulation on the paddy field after flooding.

Optionally, the environment comprises an industrial water basin, and the mollusks comprise quagga mussels or Asian clams. Optionally, the environment comprises an industrial water basin, and the mollusks comprise zebra mussels.

In another exemplary embodiment, there is presented a method of treating an environment to remediate a snail infestation that includes the steps of calculating an effective amount saponin to achieve an effective lethal dose of saponin; selecting a quantity of a formulation comprising saponin, based on the step of calculating; distributing the formulation in the environment; and allowing the saponin to disperse in the environment to cause an effective lethal concentration for the snails. In addition, maintaining an effective concentration of saponin for an exposure time to diminish or remediate the snail infestation.

Optionally, the step of maintaining an effective concentration includes maintaining an effective concentration for an exposure time of more than about 8 hours.

Optionally, the step of maintaining an effective concentration includes distributing at time intervals additional amounts of the formulation to maintain an effective concentration for an exposure time to diminish the snail infestation.

Optionally, there is selected a formulation that has a time-controlled-release of saponin. Optionally, the formulation is a tableted form.

Optionally, the method includes the steps of selecting a formulation comprising a saponin wherein the formulation is of sufficient density to sink in water and remain at the bottom of the body of water to thereby release the saponin in high concentration into the area adjacent to the bottom of the body of water. Large bodies of water such as paddy fields that are flooded are quiescent in the sense that there is little mixing other than through natural wind action or deliberate agitation. Thus, a high and lethal concentration is obtained at the bottom of the water, and saponin gradually permeates through the body of water, diluting as it permeates. Snails (or other mollusks) at the bottom encounter the high and lethal concentration being released from the dense formulation at the bottom.

In a further exemplary embodiment, there is provided a method of treating a paddy field intended to be submerged under a body of water to remediate snail infestation. The method includes the steps of: based on the volume of water to be used to submerge the paddy field, calculating an effective amount of saponin to achieve an effective lethal concentration of saponin in the volume of water; selecting a quantity of a formulation comprising saponin, based on the step of calculating; and distributing the quantity of the formulation on the area to be submerged with the volume of water. After submersion or flooding of the area with water, allowing the saponin from the distributed quantity of the formulation to disperse in the water; and maintaining an effective concentration of saponin for an exposure time to remediate the snail infestation.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

FIG. 4 is a chromatography analysis of an aqueous extract fraction of Endod showing the "peaks" that identify the presence of the molecular entities that are toxic to mollusks, and that include saponins.

DETAILED DESCRIPTION

Figure 1:
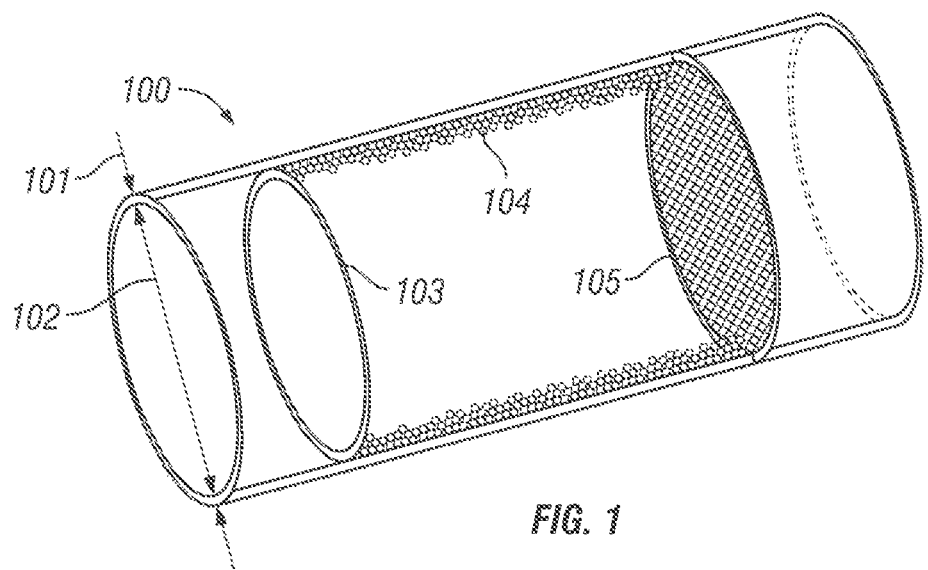
FIG. 1 is a perspective view of one embodiment of an exemplary Endod device in a disk shape.

Exemplary non-limiting embodiments are described herein. Unless otherwise noted, like elements will be identified by identical numbers throughout all figures. The invention illustratively disclosed herein suitably may be practiced in the absence of any element which is not specifically disclosed herein.

The term "remediation" as used herein with reference to a mollusk infestation includes killing the mollusks; rendering them unable to survive; rendering them incapable of latching onto surfaces, for those that are mussels or clams that must attach to a surface; reducing any residual mollusks to numbers that do not constitute an economic harm, for example in crop destruction, and negatively affecting the viability of eggs lain by mollusks, reducing the number of eggs lain by mollusks, and inhibiting egg laying by mollusks.

The term "lethal concentration" with reference to saponin means a concentration that if maintained for a sufficient duration of time will kill mollusks of the species of interest or rendering them incapable of latching onto surfaces, for those that are mussels or clams that must attach to a surface negatively affecting the viability of eggs lain by mollusks, reducing the number of eggs lain by the mollusks, and inhibiting egg laying by mollusks. It should be understood that in practice, once a concentration of saponin has been achieved in a volume of water, the saponin concentration will gradually decline over time as the saponin is degraded in the outside (non-laboratory) environment where the mollusk infestation is, in the wild. Nonetheless, an initial concentration that is high enough to kill mollusks or rendering them incapable of latching onto surfaces, for those that are mussels or clams that must attach to a surface, or negatively affecting the viability of eggs lain by mollusks, reducing the number of eggs lain by mollusks, and inhibiting egg laying by mollusks, even if it declines over time, is termed a lethal concentration. Exposure for a sufficiently long time to the concentration of saponin also plays a role in ensuring that the mollusks have a lethal dose of saponin.

The term "effective exposure time" is the time period during which there is a measurable concentration of saponin in the water to which the mollusks are being exposed.

The term "lethal dose" is a function of several variables that include both saponin concentration as well as effective exposure time. The lethal dose may be estimated for practical purposes by the area under a curve (graph) of mollusk death versus time.

The "environment" may be aquatic or on land. It is known that mollusks like snails survive well in both. If the environment is aquatic, the water may be freshwater, saltwater or brackish water. Further, the water may be considered to be potable, contaminated, or non-potable. Some snails hibernate and emerge from underground only after the soil is moistened by rain or, in the case of farming, by irrigation flooding of the land, such as rice paddies.

It has been discovered that *Phytolacca dodecandra*, generally known as African Soapberry, can be processed and used to kill certain mollusks, such as snails and mussels. For purposes of clarity, the term "Endod" is used herein to apply to dried berries and leaves of *Phytolacca dodecandra* that have been crushed to a fine powder. It has now been discovered that *Phytolacca dodecandra* is not the only source of the toxins that are lethal to mollusks. It appears that several plants, including particular fractions of an extract of these several plants, including but not limited to: quinoa (*Cheopodium quinoa*), tea plant (*Camellia sinensis*), honeysuckle (*Lonicera nigra*), akpa (*Tetrapleura tetrapluera*), thorny bone-apple (*Xeromphis spinosa*), emetic nut (*Talinum tenuissium*), kampanga (*Wsartrzia madagascariensis*), naranjito (*Swartzia simplex*), Japanese ginsing (*Panax japonicas*), tumbleweed (*Gundelia tournefortii*), English ivy (*Hedra helix*), cedar (*Polyscias dishroostachya*), soapnut (*Sapindus mukurossi*), lerak (*Sapindus rarak*), river anemone (*Anemone rivularis*), Indian horse chestnut (*Aesculus indica*), hopbush (*Dodonaea viscose*), veld lupin (*Dolichos kilimandscharicus*), munanzwa (*Albizzia anthelmintica*), glorybower (*Clerodendrum wildii*), *Lysimackia sikokiana*, and hare's ear root (*Bupleurum falcatum*) includes saponins that may possess a property of toxicity to mollusk species. In one of the exemplary embodiments, the particular toxic fraction of an aqueous extract of Endod includes saponins. This exemplary toxic fraction is shown in FIG. 4, which is a chromatographic analysis (HPLC) of an aqueous extract fraction of Endod showing the "peaks" OGTA (oleanoglycotoxin-A) and OGTB (oleanoglycotoxin-B) that identify the presence of the molecular entities that are toxic to mollusks; i.e. the peaks are markers for the efficacious extract fraction. These molecular entities include but are not limited to saponins.

In general, saponins are degradable in the environment, whether due to a multiplicity of interactive factors in the environment (heat, temperature, ultraviolet light, infrared light, water chemicals, soil chemicals, particulate matter, etc.) or not, and may be expected to have a useful active period of lethal toxicity to mollusks of interest in the range from about 4 to about 48 hours; or from 1 to about 8 hours. Of course, synthetic versions of useful saponins (or synthetic mixtures that approximate or simulate the toxic aqueous extract fraction, such as identified by the marker peaks OGTA and OGTB fraction shown in FIG. 4, for example) can also be manufactured on a large scale for large scale use. Such large scale manufacture would facilitate for example, seasonal treatment of rice paddies to remediate the infestation of Golden Apple snails (*Pomacea canaliculata*) or frequent use in municipal water supply sources or industrial water treatment basins and facilities to rid these of zebra mussels, or quagga mussels or Asian clams.

The degradability of saponins makes these chemicals suitable for use in water that is intended for agricultural or potable use. Saponins have been found safe for humans and domesticated animals. Thus, saponins can be applied in lakes, dams and rivers that are sources of irrigation water or potable water with minimal, if any, unintended adverse health or environmental impact.

Large bodies of water such as paddy fields that are flooded are quiescent in the sense that there is little vertical mixing in the water body other than through that caused by natural wind action or deliberate agitation. Thus, use of a more dense than water formulation containing saponin allows the formulation to sink to the bottom of the water. Thus, a high and lethal concentration is obtained at the bottom of the water as saponin is released from the formulation into surrounding water. The saponin gradually permeates through the body of water by concentration gradient forces, convection forces, or otherwise, diluting as it permeates. However, advantageously, snails (or other mollusks) at the bottom of the water encounter the highest and most lethal concentration being released from the dense formulation at the bottom.

Application of an appropriate concentration of saponins delivers a lethal dose to the intended mollusk that is sufficient to result in either killing the mollusk or rendering it incapable of latching onto surfaces, for those that are mussels or clams that must attach to a surface, or negatively affecting the viability of eggs lain by mollusks, reducing the number of eggs lain by mollusks, and inhibiting egg laying by mollusks. Of course, since the saponins degrade over time, if not all mollusks are killed in a first application of an amount of saponins, or if the surviving numbers are regarded as still too high, a subsequent further treatment of a concentration of saponins should be applied until there are either no survivors, or the survivors are too few to cause significant harm. It is also the case in crop protection, that the crops are most vulnerable when shoots are young and tender and are susceptible to attack by the mollusks. Once the seedlings or shoots have grown to a stage where they possess a hardier outer skin or bark, they are much less susceptible to mollusks damage. It is only critical therefore that the mollusk population be sharply curtailed during the period when the crop seedlings are tender and the crop is vulnerable to mollusk attack. Accordingly, in exemplary embodiments, pre-calculated amounts of saponin (or a formulation that includes saponin) that are estimated to cause an effective lethal concentration is applied at timed intervals to control, reduce or eliminate the mollusk infestation during the time period of interest (which may be until crop plants are no longer susceptible to mollusk attack). The time intervals for repeat applications may vary, but may be in the range of from 4 to 48 hours. In some cases the time interval between applications may be longer. For example, snails that survive may hide or find a safe place and breed. When the newly bred snails are expected to appear, at a time related to the species at issue, another treatment should be applied to kill the newly-bred snails before they mature to breed. In this way, repeated applications could eliminate snails in rice paddies, as long as snails from elsewhere do not invade the treated area. Thus, widespread treatment is advisable to minimize the risk of rapid re-infestation. Moreover, after an area has been cleared, a buffer zone that is periodically treated may be set up to surround the treated area that is free of infestation. In this way, the surrounding buffer zone may permit a treatment free zone where rice seeds may be planted, and where fish may be grown (and harvested), without adverse potential effects on the hatchling fish from residual saponin.

In an exemplary embodiment, the concentration of saponins as well as the length of application can be adjusted during the application to reach an effective lethal dose. It will be appreciated that there is interplay between dose concentration and time of exposure to the dose that causes lethality. Thus, in some environments an effective lethal dose can be at a lower concentration (ppm) of saponins along with a longer exposure time (hours), where the saponins are not as rapidly degraded. On the other hand, in an environment of rapid saponin degradation, higher saponin concentrations are necessary to take into account the inter play between lethal dose and exposure time.

In another embodiment, the formulation may comprise a component which facilitates the spread of the saponin upwards throughout a body of water that is relatively stagnant, such as a pond or basin, or a paddy field that is flooded. In this embodiment, the saponin is anticipated to rapidly be available to remediate mollusks that may inhabit numerous vertical areas of the water body. An example of such a formulation may include a composition that is effervescent in water so that the bubbling effervescence carries the saponin upward and causes mixing in the water.

With regard to Endod specifically, it can be applied in a variety of different ways. In one embodiment Soap berries are ground to form a powder. The powder can then be suspended in a liquid medium, such as water. The amount of Endod in the solution can be adjusted, but it has been found that an effective concentration of between 5 ppm and about 20 ppm has been sufficient to either kill pests or render them incapable of latching onto surfaces.

FIG. 1 is a perspective view of one embodiment of an Endod device in a disk shape. FIG. 1 shows a pipe 100. The pipe 100 can be an intake pipe, an outlet pipe, virtually any pipe through which water flows. As illustrated the pipe 100 has an outer diameter 101, and an inner diameter 102.

FIG. 1 also shows an Endod device 103. An Endod device 103 is a device which comprises Endod. The Endod can be contained within the device 103 or the Endod can be applied to the surface of the Endod device 103. In one embodiment, the Endod is applied to the device 103 via a binder. A binder is any substance which holds Endod within and/or onto the device 103. The Endod can be dissolved in the binder, or the Endod can be applied to the surface of the binder. As will be described below, in one embodiment the binder is water soluble.

As depicted the Endod device 103 comprises a disk, although the device 103 can comprise a variety of shapes. In one embodiment the device 103 has an outer diameter which is slightly less than the inner diameter 102 of the pipe 100. Slightly less refers to a first value which is between about 80% and about 100% of a second value. In one embodiment the device 103 has an outer diameter which is between about 90% and about 100% of the inner diameter 102 of the pipe 100.

As depicted the device 103 is a disk which has a central opening. In other embodiments the disk comprises two or more openings. In still other embodiments the device 103 does not comprise a central opening but instead is water permeable. In such an embodiment water flows through the device 103. In one embodiment the shape of the device 103 is substantially similar to the cross-section of the pipe 100. In other embodiments the device 103 comprises the shape of a cube, ball, or other solid surface. The device 103 can comprise virtually any shape.

As noted, in one embodiment the device 103 comprises Endod. In one embodiment the Endod device 103 comprises a slow release Endod device. As used herein, a slow release Endod device is a device which is still releasing Endod after 2 hours. In one embodiment the slow release Endod is still releasing Endod after 8 hours. The time release properties of the Endod on the device 103 can be adjusted for a variety of factors including the size of the pipe, the flow rate through the pipe, the length of the pipe, etc. It can be appreciated that if all of the Endod was simply released at a single point, the Endod would disperse through and with the flowing fluid. As such, the residence time of the Endod within the pipe and around the pests would be minimal. However, a slow release allows some Endod to be released over time which increases the time in which the pests are exposed to Endod, referred to herein as the exposure time.

It has been discovered that some mussels and other such pests can sense chlorine and other chemicals in the water. When this happens, the pests do not circulate or otherwise take-in air and/or water for a period of between 1 and 8 hours. Accordingly, in one embodiment the duration of the application of the Endod is greater than 8 hours. This ensures the exposure time will be greater than the time that the pests do not circulate air/water. Consequently, the pest will be exposed to Endod. As such, in one embodiment the slow release properties of the disk allow the Endod to be released for a period greater than 8 hours.

The time release properties of the Endod and the device 103 can be achieved in a variety of ways. In one embodiment the Endod is encapsulated in the device 103 via a binder. As noted, in one embodiment the binder comprises a water soluble substance. Thus, as the water soluble substance dissolves over time, the Endod which was encapsulated or otherwise sealed by the water soluble substance is released. The water soluble substance can comprise any substance which slowly dissolves in water and which is non-reactive to the Endod. Examples of such a water soluble substance includes but is not limited to some salts and sugars.

Figure 2:
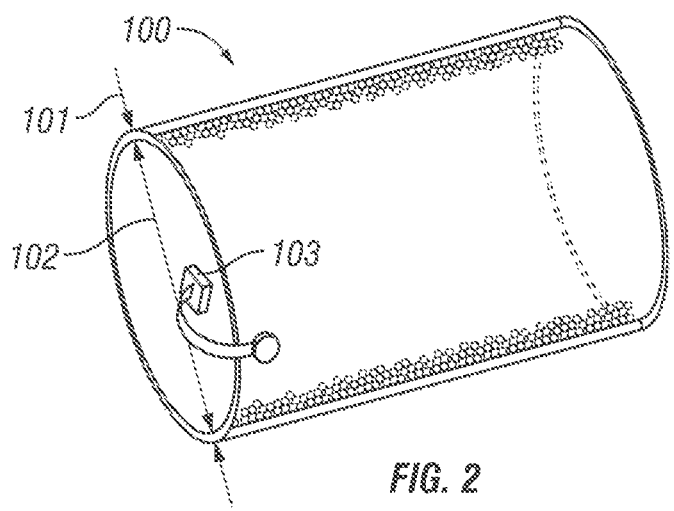
FIG. 2 is a perspective view of an Endod device in one embodiment.

In one embodiment the device 103 is a permanent feature secured temporarily to a location upstream of the pests which are to be removed. For example, the device 103 can be located near the intake of the pipe 100. FIG. 2 illustrates a perspective view of an Endod device in one embodiment. The device 103 can be secured via any device known in the art including welding, screwing, bolting, etc. Thus, water flows around and/or through the device 103 and distributes the Endod to the pests 104.

Referring back to FIG. 1 it can be seen that the device 103 comprises a disk shape. As noted, in one embodiment the outer diameter of the device 103 is slightly less than the inner diameter of the pipe 100. In one embodiment the device 103 operates as previously described by releasing Endod over time. Thus, the pests 104 of this embodiment are removed via a chemical means. However, in one embodiment the device 103 further provides a mechanical force to remove the pests. As seen in FIG. 1, water applies a force against the device 103 in an attempt to push the device 103 downstream. As the device 103 is forced downstream it slowly releases Endod. Simultaneously, while advancing downstream the device 103 brushes against the inner diameter 102 of the pipe 100. While advancing downstream, however, the device 103 is stopped by the presence of mussels 104 which have yet to release. Put differently, the device 103 cannot advance downstream because pests 104 block the device's 103 further movement. As such, the force of the water pressed against the downstream end of the device 103 which applies a force against the pests 104. The obstructing pests 104 become weak due in part to the presence of the Endod as well as the pressure of the device 103. Thus, the obstructing pests 104 eventually lose their grip and fall. The device 103 is then advanced further downstream where it may or may not abut against additional obstructing pests 104.

As noted, in one embodiment the Endod device 103 maintains its shape as it advances through the pipe 100. As such, in one embodiment the Endod device 103 comprises sufficient rigidity to retain its shape. In such embodiments, this rigidity prevents the Endod device 103 from contorting. Accordingly, the Endod device 103 maintains its shape and thus advances along the inside diameter of the pipe 100. Without sufficient rigidity, the Endod device 103 could bend and flow through the pipe 100 without encountering any obstructing pests 104.

As described there are several methods of treating pests utilizing an Endod device. In one embodiment an Endod device is first obtained. Thereafter, the Endod device is placed in a pipe. In one embodiment the device is secured within the pipe. In other embodiments the Endod device is advanced downstream through the pipe.

This method offers several unexpected benefits. First, this method allows the combination of mechanical and chemical means to remove the pests. Further, in one embodiment because the released Endod is in close proximity with the obstructing mussel, the obstructing mussel receives a high concentration blast of Endod. This is because the Endod has not yet had an opportunity to diffuse within the flowing water. Thus, the obstructing pests receive a concentrated blast of Endod as well as an applied force of the device 103. The combined forces ensure the pests release their grip.

Another benefit is that, in some embodiments, when the device 103 reaches any downstream location, the operator is ensured that the pipe surfaces upstream of the device 103 have been successfully cleaned. As an example, in FIG. 1 the pipe comprises a removable filter 105. A filter prevents larger items from passing downstream of the filter. For example, if FIG. 1 shows the intake to a pump it may be desirable to minimize the passage of any large items to the pump. A removable filter 105 helps trap items of a specified size from flowing downstream of the filter. Any filter 105 known in the art can be used. As noted above, if the device 103 is stopped at the filter 105, then the operator knows that the pipe 100 upstream of the filter 105 has been successfully cleaned. The filter 105 can also act to capture released pests. It should be noted that in some embodiments the entire Endod device 103 is water soluble.

Figure 3:
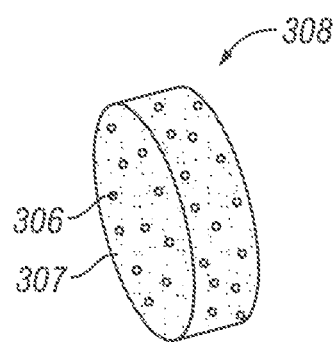
FIG. 3 is a perspective view of an Endod tablet in one embodiment.

FIG. 3 is a perspective of an Endod tablet in one embodiment. In this embodiment the tablet 308 comprises Endod 306 as well as a water soluble binder 307. In operation the tablet 308 is dropped into a body of water comprising pests. In one embodiment the tablet 308 is a time release tablet which releases Endod over time. In one embodiment the tablet 308 is still releasing Endod after 8 hours. The water soluble substance 307 can comprise any water soluble substance previously described. The amount of Endod 306 per tablet can be adjusted for a variety of factors.

In operation at least one tablet 308 is inserted within a body of water comprising pests. The tablet 308 releases the Endod 306 which subsequently kills the pests or renders them incapable of latching onto solid surfaces. In one embodiment the first step is determining the amount of Endod required for an effective application. In one embodiment the first step comprises determining the approximate volume of water to be treated. Thereafter, the proper amount of tablets 308 is inserted into the water.

As noted, there are several unexpected results. First, removing undesirable pests from solid surfaces resulted in increased flow though pipes, better functioning ballasts, and cleaner solid surfaces. Additionally, killing disease carrying pests prevents the spreading of many diseases. Finally, because Endod is safe for the environment and humans, any unintended environmental concerns are minimized.

In still another embodiment pipes and other items, such as a ship's ballast, are pre-treated with Endod. For example, a pipe can be coated with a slow release coating which comprises Endod. In one embodiment the slow release coating slowly releases Endod for a period of many months. In such embodiments the pre-coated pipes would prevent the accumulation of pests. This method can be supplemented with the other methods and devices discussed herein.

While the invention has been particularly shown and described with reference to exemplary embodiments, these do not limit the scope of the inventions. It will be understood by those skilled in the art that various changes in form and detail may be made therein without departing from the spirit and scope of the inventions, which are defined only by the attached patent claims as interpreted by a court of competent jurisdiction.

What is claimed is:

1. A method of treating an environment having an infestation of mollusks, either active or in hibernation, to remediate a mollusk infestation, the method comprising the steps of:
   a. selecting an amount of a formulation comprising a molluscicide including oleanoglycotoxin-A or oleanoglycotoxin-B, or both;
   b. treating the environment by distributing the formulation in the environment having an infestation of mollusks, the mollusks either active or not;
   c. allowing the molluscicide to disperse in water, the water submerging the environment, to thereby cause an effective lethal dose of the molluscicide in the water;
   d. maintaining a concentration of the molluscicide in the water for an exposure time sufficient to remediate the mollusk infestation, and
   e. sequentially, at time intervals, treating the environment by again distributing the formulation in the environment to kill mollusks, including mollusks newly emerging in or migrating into the environment.

2. The method of claim 1, wherein step (d) of maintaining the concentration of molluscicide comprises distributing an additional amount of the formulation.

3. The method of claim 1, wherein step (d) comprises maintaining a concentration of molluscicide for an exposure time of about 1 to about 48 hours.

4. The method of claim 1, wherein step (d) comprises maintaining a concentration of molluscicide for an exposure time of about 1 to about 8 hours.

5. The method of claim 1, wherein step (a) comprises selecting a formulation comprising molluscicide and a binder.

6. The method of claim 1, wherein step (a) comprises selecting a formulation comprising a synthetic molluscicide.

7. The method of claim 1, wherein the formulation is in a solid form.

8. The method of claim 7, wherein the formulation has a time-controlled release of molluscicide.

9. The method of claim 1, wherein the mollusks comprise snails.

10. The method of claim 1, wherein the environment comprises a rice paddy field wherein the mollusks comprise snails, and wherein the step (b) comprises distributing the formulation on the rice paddy field after flooding, and wherein the formulation sinks in water.

11. The method of claim 1, wherein the environment comprises a rice paddy field wherein the mollusks comprise snails, and wherein the step (b) comprises distributing the formulation on the rice paddy field before planting rice seedlings.

12. The method of claim 11, further comprising a step of distributing the formulation in buffer areas around the rice paddy field, and periodically treating the buffer areas by distributing the formulation until rice plants are able to withstand a snail predation.

13. The method of claim 11, wherein the step (e) of treating by distributing the formulation on the rice paddy field is repeated periodically until rice plants are able to withstand a snail predation.

14. The method of claim 1, wherein the formulation is in a liquid form.

15. The method of claim 1, wherein step (b) comprises selecting a formulation that includes an effervescent composition.

16. A method of treating a paddy field intended to be submerged under a body of water to remediate snail infestation, the method comprising the steps of:
   a. determining an effective amount of molluscicide comprising oleanoglycotoxin-A or oleanoglycotoxin-B, or both, to achieve an effective lethal concentration of molluscicide in a volume of water to submerge the paddy field;

b. distributing the determined effective amount of the molluscicide on the paddy field to be submerged with the volume of water;

c. treating the paddy field by submerging under water to disperse the molluscicide from the distributed effective amount of the formulation in the water;

d. maintaining a concentration of the molluscicide in the water for an exposure time to remediate the snail infestation; and e. sequentially, after an elapsed time, again treating the paddy field by distributing the formulation in the paddy field to kill mollusks, including mollusks newly emerging in or migrating into the environment.

17. The method of claim 16, wherein a step of planting rice seedlings follows the step (e) of treating.

18. The method of claim 16, wherein a step of planting or sowing rice seeds is after the step (b) of distributing the formulation, and before the step of submerging the paddy field.

19. The method of claim 16, wherein a step of planting rice seedlings follows the step (c) of treating.

20. The method of claim 16, further including a step of treating a buffer area around the paddy field with an effective amount of molluscicide periodically to minimize snail incursion into the paddy field through the buffer area.

21. A method of treating a paddy field intended to be submerged under a body of water to remediate snail infestation, the method comprising the steps of:

a. determining an effective amount of a molluscicide comprising oleanoglycotoxin-A or oleanoglycotoxin-B, or both, to achieve an effective lethal concentration of the molluscicide in a volume of water to submerge the paddy field;

b. treating the paddy field by submerging under water to disperse the molluscicide from the distributed effective amount of the molluscicide in the water; and c. sequentially, at time intervals again treating the environment by distributing the molluscicide in the environment to kill mollusks, including mollusks emerging in or migrating into the submerged paddy field, until rice plants in the paddy field are able to withstand snail predation.

22. The method of claim 21 further comprising, after the treating and submerging of step (b), planting rice seedlings.

23. The method of claim 21 further comprising, after the sequentially treating of step (c), planting rice seedlings.

24. The method of claim 21, further comprising, after step (c), planting rice seeds.

25. The method of claim 21, further including a step of treating a buffer area around the paddy field with an effective amount of molluscicide periodically to minimize snail incursion into the paddy field through the buffer area.

* * * * *